US009045283B2

(12) United States Patent (10) Patent No.: US 9,045,283 B2
Matsunoshita (45) Date of Patent: Jun. 2, 2015

(54) OBJECT INFORMATION MANAGEMENT SYSTEM AND PROGRAM

(71) Applicant: FUJI XEROX CO., LTD., Minato-ku, Tokyo (JP)

(72) Inventor: Junichi Matsunoshita, Yokohama (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 14/169,948

(22) Filed: Jan. 31, 2014

(65) Prior Publication Data

US 2014/0148943 A1     May 29, 2014

Related U.S. Application Data

(63) Continuation of application No. PCT/JP2012/050110, filed on Jan. 5, 2012.

(30) Foreign Application Priority Data

Sep. 16, 2011   (JP) .................................. 2011-202702

(51) Int. Cl.
    *G06F 7/00*      (2006.01)
    *B65G 1/02*      (2006.01)
    *G06Q 30/00*     (2012.01)

(52) U.S. Cl.
    CPC .............. *B65G 1/02* (2013.01); *G06Q 30/0185* (2013.01)

(58) Field of Classification Search
    CPC ...................................................... G06Q 10/08
    USPC ........................................................ 700/215
    See application file for complete search history.

(56) References Cited

U.S. PATENT DOCUMENTS 7,865,124 B2 *   1/2011   Piersol et al. ................. 399/361
(Continued)

FOREIGN PATENT DOCUMENTS

CN         1577355 A      2/2005
CN         101006555 A    7/2007
(Continued)

OTHER PUBLICATIONS

Communication dated Feb. 4, 2015, issued by the State Intellectual Property Office of the People's Republic of China in corresponding Chinese Application No. 201280043589.2.

*Primary Examiner* — Gene Crawford
*Assistant Examiner* — Kyle Logan
(74) *Attorney, Agent, or Firm* — Sughrue Mion, PLLC

(57)   ABSTRACT

An object information registration device (100) acquires peculiar image information obtained by imaging surface patterns of objects at predetermined imaging spots before the objects are stored in containers and imaging time instants so as to be associated with respective objects having peculiar patterns on surfaces respectively in a manufacturing process of the objects, acquires container identification information identifying the containers containing the objects and time ranges in which the objects are stored in the containers so as to be associated with each other and registers the container identification information corresponding to the obtained peculiar image information so as to be associated with respective objects based on a time difference from the imaging of the objects to the storing in the container, the imaging time instants associated with the peculiar image information of the objects and the time ranges associated with container identification information of containers containing the objects.

8 Claims, 6 Drawing Sheets

(56) References Cited

U.S. PATENT DOCUMENTS

| | | |
|---|---|---|
| 2004/0267677 A1 | 12/2004 | Mitsuoka et al. |
| 2008/0106714 A1 | 5/2008 | Okita |
| 2009/0073517 A1* | 3/2009 | Kuroda ............... 358/505 |
| 2009/0110295 A1 | 4/2009 | Ogaki et al. |
| 2009/0276082 A1 | 11/2009 | Murata |
| 2010/0290671 A1* | 11/2010 | Shimizu ............... 382/103 |

FOREIGN PATENT DOCUMENTS

| | | |
|---|---|---|
| CN | 101151197 A | 3/2008 |
| JP | 2004-85212 A | 3/2004 |
| JP | 2005010581 A | 1/2005 |
| JP | 2007015704 A | 1/2007 |
| JP | 2009109419 A | 5/2009 |
| JP | 2010143660 A | 7/2010 |

* cited by examiner

FIG.3

| MANUFACTURING LINE ID | IMAGING APPARATUS ID | DISTANCE | CONVEYANCE SPEED |
|---|---|---|---|
| 20-1 | 30A-1 | $d_A$ | $s_A$ |
| ⋮ | ⋮ | ⋮ | ⋮ |
| 20-M | 30A-M | $d_M$ | $s_M$ |
|  |  |  |  |

FIG.4

| OBJECT ID | SURFACE PATTERN INFORMATION | IMAGING TIME | IMAGING APPARATUS ID |
|---|---|---|---|
| 0001 | P0001 | $t_1$ | 30A-1 |
| 0002 | P0002 | $t_2$ | 30A-2 |
| 0003 | P0003 | $t_3$ | 30A-M |
|  |  |  |  |

FIG.5

| CONTAINER ID | ORIGINAL CONTAINER ID | READING START TIME | READING END TIME | IMAGING APPARATUS ID |
|---|---|---|---|---|
| B0001 | — | $t_{11}$ | $t_{12}$ | 30B-1 |
| B0002 | — | $t_{13}$ | $t_{14}$ | 30B-1 |
| B0003 | — | $t_{15}$ | $t_{16}$ | 30B-1 |
| B0004 | B0001 | $t_{17}$ | $t_{18}$ | 30B-2 |
|  |  |  |  |  |

FIG.6

| OBJECT ID | SURFACE PATTERN INFORMATION | CONTAINER ID | MANUFACTURE INFORMATION |
|---|---|---|---|
| 0001 | P0001 | B0001<br>B0004 | 20-1 |
| 0002 | P0002 | B0001<br>B0004 | 20-2 |
| 0003 | P0003 | B0002 | 20-M |
| | | | |

FIG.7

| CONTAINER ID | SHIPPING DESTINATION | SHIPPING DATE | VEHICLE ID |
|---|---|---|---|
| B0004 | A HOSPITAL | $t_{1001}$ | C0001 |
| B0005 | B HOSPITAL | $t_{1002}$ | C0002 |
| | | | |

OBJECT INFORMATION MANAGEMENT SYSTEM AND PROGRAM

CROSS-REFERENCE TO RELATED APPLICATIONS

The present application is a National Stage of International Application No. PCT/JP2012/050110 filed Jan. 5, 2012, claiming priority from Japanese application JP 2011-202702 filed on Sep. 16, 2011, the contents of all of which are incorporated herein by reference in their entirety.

BACKGROUND

Technical Field

The present invention relates to an object information management system, an object information management method and a non-transitory computer readable medium.

SUMMARY

According to an aspect of the invention, there is provided an object information management system including an object information acquisition unit that acquires peculiar image information obtained by imaging surface patterns of objects at predetermined imaging spots before the objects are stored in containers and imaging time instants so as to be associated with respective objects having peculiar patterns on surfaces respectively in a manufacturing process of the objects; a container information acquisition unit that acquires container identification information identifying the containers containing the objects and time ranges in which the objects are stored in the containers so as to be associated with each other; and a registration unit that registers the container identification information corresponding to peculiar image information acquired by the object information acquisition unit so as to be associated with respective objects based on a time difference from the imaging of the objects to the storing in the container, the imaging time instants associated with the peculiar image information of the objects and the time ranges associated with container identification information of containers containing the objects.

BRIEF DESCRIPTION OF THE DRAWINGS

An exemplary embodiment of the present invention will be described in detail based on the following figures, wherein:

FIG. 3 is a chart showing an example of data of manufacturing lines;

FIG. 4 is a chart showing an example of a surface pattern information table;

FIG. 5 is a chart showing an example of a container information table;

FIG. 6 is a chart showing an example of a corresponding information table;

FIG. 7 is a chart showing an example of a shipping information table;

DETAILED DESCRIPTION

Hereinafter, an exemplary embodiment for carrying out the invention (hereinafter referred to an embodiment) will be explained with reference to the drawings.

Figure 1:
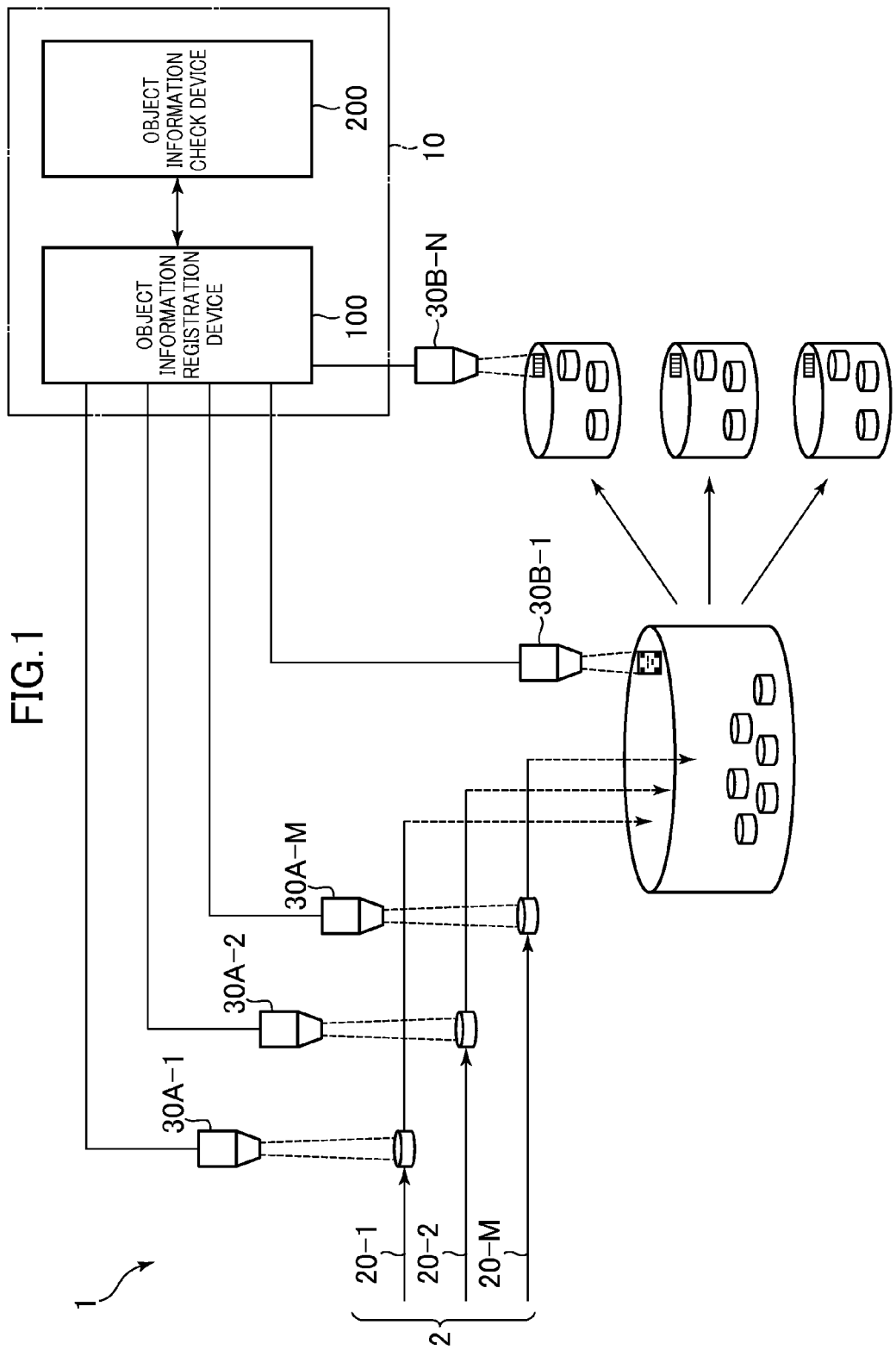
FIG. 1 shows a system configuration diagram of an object processing system according to an embodiment.

FIG. 1 shows a system configuration diagram of an object processing system 1 according to this embodiment. As shown in FIG. 1, the object processing system 1 includes a manufacturing system 2 manufacturing objects and an object information management system 10 reading surface pattern information (fingerprint information) peculiar to individual objects manufactured in the manufacturing system 2, information of containers containing the objects and so on and managing these information. Here, objects may have peculiar surface patterns. For example, pills, electronic components and so on can be cited.

The manufacturing system 2 includes manufacturing lines 20-1 to M (M is an integer larger than 1) in which objects (pills) are manufactured. Hereinafter, regarding the contents common to the manufacturing lines 20-1 to M, the manufacturing line 20 will be used. In the manufacturing line 20 according to the embodiment, after pills are manufactured, the manufactured pills are sequentially stored in first to Nth (N is an integer larger than 1) container and the Nth container is shipped. As N=2 in the example shown in FIG. 1, the manufactured pills are gathered in the first container (lot), then, divided in the second container (bottles, shipping containers), and the second container is shipped. Naturally, the number of N is not limited to the example shown in FIG. 1. For example, when N=1, the manufactured pills may be stored in the first container (bottles, shipping containers), and the first container may be shipped.

The object information management system 10 acquires surface pattern information of objects and information of containers in which the objects are stored and manages the information during a period from the manufacture to the shipping of the objects (pills). The object information management system 10 according to the embodiment includes an object information registration device 100 and an object information check device 200. The object information registration device 100 is connected to imaging apparatuses 30A-1 to M, 30B-1 to N. Hereinafter, the details of the imaging apparatuses 30A-1 to M, 30B-1 to N and respective devices included in the object information management system 10 will be explained. Regarding the contents common to the imaging apparatuses 30A-1 to M, the imaging apparatus 30A will be used. Regarding the contents common to the imaging apparatuses 30B-1 to N, the imaging apparatus 30B will be used.

The imaging apparatuses 30A-1 to M are imaging apparatuses reading surface pattern information of objects (pills) during a period from manufacture of objects (pills) in the manufacturing line 20 until the objects are stored in the first container. The imaging apparatuses 30B-1 to N are imaging apparatuses reading identification information (container IDs) for respectively identifying individual first to Nth containers in which pills manufactured in the manufacturing line 20 are stored.

The respective imaging apparatuses 30A-1 to M as well as the imaging apparatuses 30B-1 to N output the read information and time instants at which the information is read to the object information registration device 100. The imaging apparatuses 30A-1 to M may be provided so as to correspond to the manufacturing lines 20-1 to M and may image surfaces of objects (pills) with resolution of, for example, approximately 600 dpi to thereby obtain a predetermined size (for example, 32×32 dot) as the surface pattern information. The imaging apparatuses 30B-1 to N may read code information such as barcode and two-dimensional code information obtained by encoding identification information added to the containers. In the embodiment, during a period in which the same container ID is read by, for example, the imaging apparatuses 30B-i (i=1 to N), a work (feeding work) of storing pills into containers identified by the container ID is performed.

The object information registration device 100 registers information of objects (pills) and containers in which the objects (pills) are stored so as to be associated with each other based on information inputted from the imaging apparatus 30A and the imaging apparatus 30B. Specifically, the object information registration device 100 receives inputs of surface pattern information obtained by imaging respective objects (pills) and imaging time instants from the imaging apparatus 30A as well as receives inputs of container IDs read with respect to respective containers and time instants at which the container IDs have been read (storing time instants of pills with respect to containers). Then, the object information registration device 100 specifies container IDs with which surface pattern information (basic pattern information) should be associated based on a time difference between the imaging time instant and the storing time instant with respect to the container in the manufacturing line 20 in which the objects are manufactured, registering the specified surface pattern information and the container IDs so as to be associated with each other.

The object information check device 200 receives an identification request including surface pattern information (target pattern information) and the container ID of an object as an identification target from a not-shown client apparatus. Then, the object information check device 200 extracts the surface pattern information registered so as to be associated with the received container ID by the object information registration device 100 as check candidates, and checks the extracted surface pattern information of the check candidates with the target pattern information, thereby specifying surface pattern information corresponding to the target pattern information. When corresponding surface pattern information is specified by the above process, the object information check device 200 provides information stored by being associated with the surface pattern information to the client apparatus as a check result, and when the corresponding surface pattern is not specified, the object information check device 200 may provide information indicating the fact to the client apparatus as a check result.

Hereinafter, the details of functions included in the object information registration device 100 and the object information check device 200 will be explained with reference to respective functional block diagrams of the object information registration device 100 and the object information check device 200 shown in FIG. 2.

First, functions included in the object information registration device 100 will be explained. As shown in FIG. 2, the object information registration device 100 includes a storage unit 102, a surface pattern information acquisition unit 104, a container information acquisition unit 106, a time difference calculation unit 108, an information associating unit 110 and a shipping information registration unit 112.

The functions of respective units included in the object information registration device 100 may be realized by a computer which has a control unit such as a CPU, a storage unit such as a memory, an input/output unit for transmitting and receiving data with respect to external devices and so on reading and executing a program stored in a computer-readable information storage medium. The program may be supplied to the object information registration device 100 included in the computer by information storage media such as an optical disc, a magnetic disc, a magneto-optical disc and a flash memory, and may also be supplied to the object information registration device 100 through data communication networks such as Internet.

The storage unit 102 is realized by a hard disk or a semiconductor memory, storing data and programs. The storage unit 102 stores previously stored data, data inputted from the imaging apparatuses 30A, 30B and the like.

FIG. 3 shows an example of data of the manufacturing line 20 as one of data stored in the storage unit 102. As data of the manufacturing line 20 shown in FIG. 3, the manufacturing line ID identifying each manufacturing line 20 included in the object processing system 1, the imaging apparatus ID identifying the imaging apparatus 30A installed in each manufacturing line 20, the distance from a position where the imaging apparatus 30A is installed in each manufacturing line 20 to the position where the objects (pills) are stored in the container and the conveyance speed of each manufacturing line 20 are stored so as to be associated with one another.

The surface pattern information acquisition unit 104 acquires surface pattern information obtained by imaging surface patterns of objects (pills) manufactured in the manufacturing line 20 from the imaging apparatus 30A. In this embodiment, the surface pattern information acquisition unit 104 sequentially acquires imaged surface pattern information and imaging time instants from the imaging apparatus 30A, and sequentially stores the acquired information in the storage unit 102.

FIG. 4 shows an example of a surface pattern information table storing surface pattern information acquired by the surface pattern information acquisition unit 104. In the surface pattern information table shown in FIG. 4, the object ID identifying respective objects (pills), the surface pattern information of respective objects, the imaging time instant at which the surface pattern information is imaged and the imaging apparatus ID of the imaging apparatus 30A which has imaged the surface pattern information are stored so as to be associated with one another.

The container information acquisition unit 106 acquires identification information of containers containing objects (pills) from the imaging apparatus 30B. In the embodiment, the container information acquisition unit 106 may acquire container information including container IDs read by the imaging apparatus 30B-i (i=1 to N) and read time instants of the container IDs and may store the acquired container information in the storage unit 102. At this time, the container information acquisition unit 106 may acquire both the container ID (original container ID) of an original container (the i-th container) from which objects (pills) are moved and the container ID of a destination container (the i-th +1 container) to which objects (pills) are moved (for example, to be repackaged).

FIG. 5 shows an example of a container information table storing container information acquired by the container information acquisition unit 106. In the container information table shown in FIG. 5, the container ID identifying respective containers, the original container ID identifying an original container in which objects to be stored in the container have been stored before, the reading start time instant of the container ID (feeding start time instant of objects to the container), the reading end time instant of the container ID (feeding end time instant of objects to the container) and the imaging apparatus ID of the imaging apparatus 30B which has read the container ID are stored so as to be associated with one another.

The time difference calculation unit 108 calculates the time difference of movement from an imaging position at which the object is imaged by the imaging apparatus 30A arranged in the manufacturing line 20 to a storing position at which the object is stored in the container. For example, the time difference calculation unit 108 may calculate a period of time obtained by dividing the distance from the imaging position to the storing position by the conveyance speed as the time difference in each manufacturing line 20 based on data of the manufacturing line 20 shown in FIG. 3 which is stored in the storage unit 102.

The information associating unit 110 associates the surface pattern information acquired by the surface pattern information acquisition unit 104 and the container information (container ID) acquired by the container information acquisition unit 106 based on the time difference calculated by the time difference calculation unit 108. For example, the information associating unit 110 specifies the container ID in which a period of time obtained by adding the imaging time instant associated with the object ID in the surface pattern information table to the time difference calculated in the time difference calculation unit 108 concerning the manufacturing line 20 manufacturing the object of the object ID is within a feeding time range (from the feeding start time instant to the feeding end time instant) in the container IDs relating to the first container in the container information table (the ID of the container to which objects are directly fed from the manufacturing line 20 and read by the imaging apparatus 30B1), and registers the specified container ID and the object ID in the storage unit 102 so as to be associated to each other. Furthermore, the information associating unit 110 executes processing of searching a record having the container ID associated with the object ID as the original container ID from the container information table, and registering the container ID included in the searched record in the storage unit 102 by further associating the container ID with the object ID until no new records are searched.

FIG. 6 shows an example of a corresponding information table registered in the storage unit 102 by the information associating unit 110. In the corresponding information table shown in FIG. 6, the object ID, the surface pattern information, the first to the N-th container ID and the manufacture information such as the manufacturing line ID are stored so as to be associated with one another. The i-th (i=1 to N) container IDs indicates a group of container IDs respectively read by the imaging apparatus 30B-i, and specifically, the first container ID includes container IDs of containers to which objects are directly fed from the manufacturing line 20, and the N-th container ID includes container IDs of containers for shipping (shipping containers). The manufacture information may include not only the manufacturing line ID but also the manufacture place (factory name), the manufacture date, identification information of workers (worker's names, worker IDs and so on).

The shipping information registration unit 112 registers shipping information concerning objects manufactured in the manufacturing line 20 in the storage unit 102. The shipping information may include, for example, information of shipping destinations of shipping containers containing objects, information of shipping dates, identification information of transporting vehicles (vehicle IDs) transporting containers and so on.

FIG. 7 shows an example of a shipping information table registered by the shipping information registration unit 112. In the shipping information table shown in FIG. 7, the container ID of the shipping container, the shipping destination, the shipping date and the vehicle ID are stored so as to be associated with one another.

Next, the details of functions included in the object information check device 200 will be explained with reference to the functional block diagram shown in FIG. 2.

Figure 2:
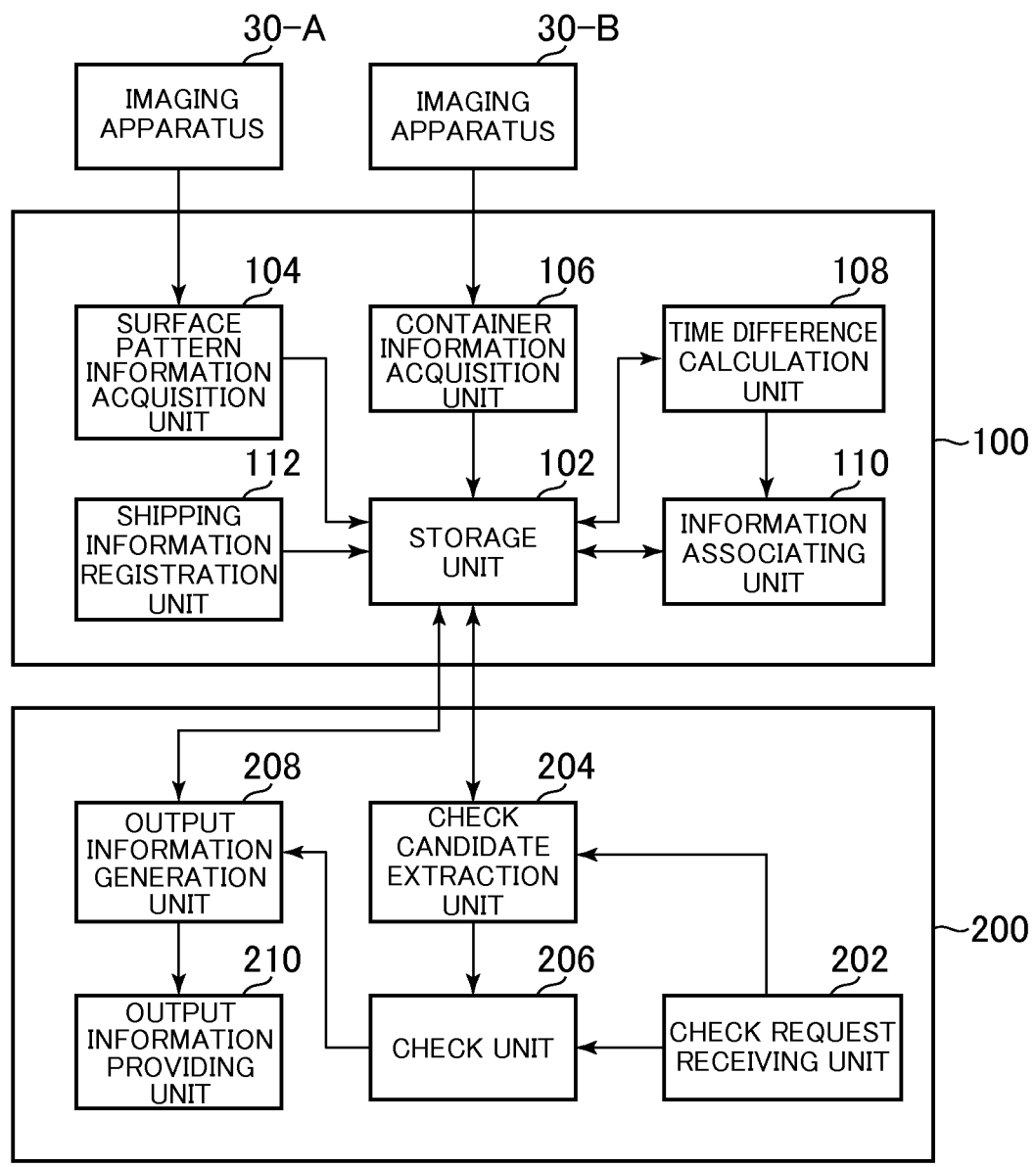
FIG. 2 shows respective functional block diagrams of an object information registration device and an object information check device.

As shown in FIG. 2, the object information check device 200 includes a check request receiving unit 202, a check candidate extraction unit 204, a check unit 206, an output information generation unit 208 and an output information providing unit 210.

The functions of respective units included in the object information check device 200 may be realized by a computer which has a control unit such as a CPU, a storage unit such as a memory, an input/output unit for transmitting and receiving data with respect to external devices and so on reading and executing a program stored in a computer-readable information storage medium. The program may be supplied to the object information check device 200 included in the computer by information storage media such as an optical disc, a magnetic disc, a magnetic tape, a magneto-optical disc and a flash memory, and may also be supplied to the object information check device 200 through data communication networks such as Internet.

The check request receiving unit 202 receives a check request including surface pattern information (target pattern information) and/or the container ID of the identification target from the client apparatus.

The check candidate extraction unit 204 extracts surface pattern information stored in the storage unit 102 by being associated with the container ID as candidates to be checked with target pattern information based on the container ID received from the check request receiving unit 202. Specifically, the check candidate extraction unit 204 searches records including the container ID received by the check request receiving unit 202 from the corresponding information table stored in the storage unit 102 and extracts surface pattern information included in the searched records as candidates to be checked with the target pattern information.

The check unit 206 checks target pattern information received by the check request receiving unit 202 and surface pattern information of the candidates extracted by the check candidate extraction unit 204 respectively, determining whether there is information corresponding to (matching) the target pattern information in the surface pattern information of candidates. Then, the check unit 206 outputs the check result to the output information generation unit 208.

The output information generation unit 208 generates output information to be provided to the client apparatus based on the check result inputted from the check unit 206. For example, when surface pattern information corresponding to the target pattern information has been obtained by the check unit 206, the output information generation unit 208 may include information associated with the surface pattern information (for example, information of a manufacturing factory, information of the manufacturing line 20, information of a manufacturing date, shipping information and so on) in output information. When surface pattern information corresponding to the target pattern information has not been obtained by the check unit 206, the output information generation unit 208 may include the fact that there is a possibility that the target object (pill) has not been manufactured in managed factories in output information.

The output information providing unit 210 provides output information generated by the output information generation unit 208 to the client apparatus. For example, the output information providing unit 210 may transmit the generated output information to the client apparatus.

Next, the flow of processing performed in the object information management system 10 will be explained with reference to flowcharts shown in FIG. 8 and FIG. 9.

Figure 8:
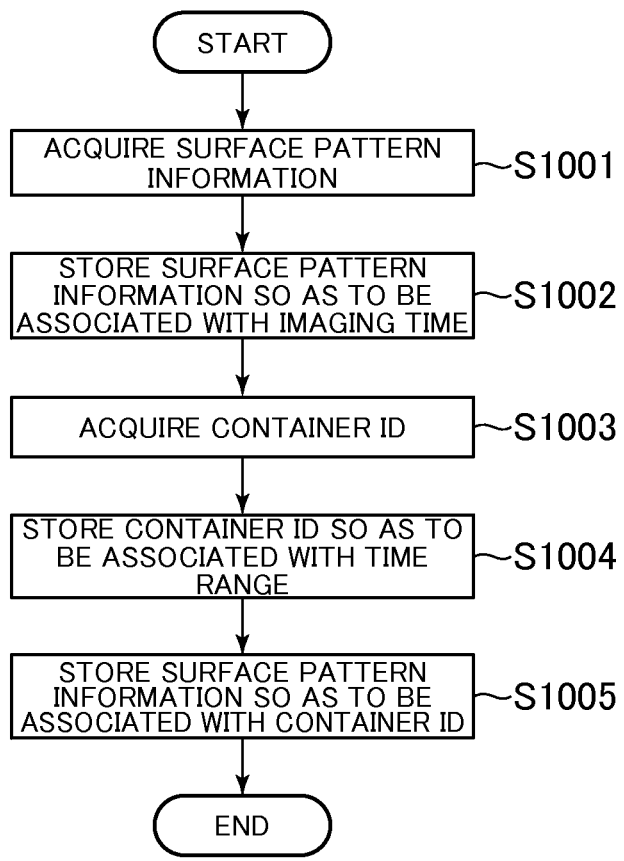
FIG. 8 shows an example of a flowchart of registration processing.

FIG. 8 shows an example of a flowchart of registration processing. As shown in FIG. 8, the object information registration device 100 acquires surface pattern information obtained by imaging a surface pattern of an object manufactured in the manufacturing line 20 from the imaging apparatus 30A (S1101) and stores the acquired surface pattern so as to be associated with an imaging time instant (S1002).

Next, the object information registration device 100 acquires identification information of a container (container ID) read by the imaging apparatus 30B in a process of storing objects manufactured in the manufacturing line 20 in the container (S1003), storing the acquired identification information (container ID) so as to be associated with a time range in which the identification information is read (S1004).

The object information registration device 100 stores the acquired surface pattern information and the container ID so as to be associated with each other in a database based on the time difference from the imaging of the object to the storing in the container (S1005) and ends the processing.

Figure 9:
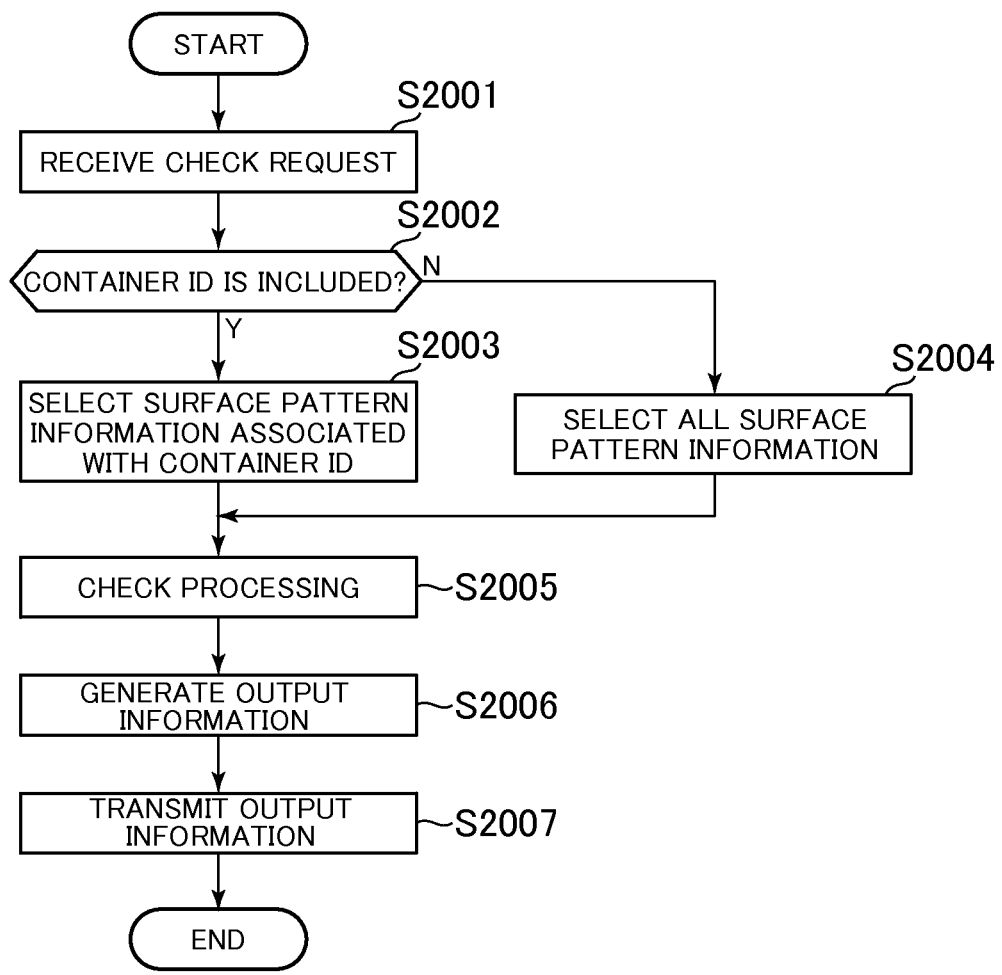
FIG. 9 shows an example of a flowchart of check processing.

FIG. 9 shows an example of a flowchart of check processing. As shown in FIG. 9, the object information check device 200 receives a check request including surface pattern information of the identification target (target pattern information) from the client apparatus (S2001). Here, when the container ID is included in the received check request (S2002: Y), the object information check device 200 selects surface pattern information stored in the database so as to be associated with the container ID as check candidates (S2003). On the other hand, when the container ID is not included in the check request received by the object information check device 200 in S2002 (S2002: N), the object information check device 200 selects all surface pattern information stored in the database as check candidates (S2004).

The object information check device 200 checks the selected surface pattern information of check candidates with the target pattern information respectively (S2005), generating output information based on the check result (S2006) and transmitting the output information to the client apparatus (S2007) to end the processing.

In the object information management system 10 explained as the above, surface pattern information peculiar to individual objects and identification information identifying containers containing individual objects are registered so as to be associated with each other at the time of manufacturing objects, and the number of surface pattern information to be checked with the target object can be narrowed down by using the identification information of containers containing the target object, thereby reducing the processing load.

The present invention is not limited to the above embodiment. For example, the storage unit 102 of the object information registration device 100 can be provided as a database server separately from the object information registration device 100 and the object information check device 200, as well as the object information registration device 100 and the object information check device 200 can be provided as an integral device.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

The invention claimed is:

1. An object information management system comprising:
    an object information acquisition unit configured to acquire surface pattern image information obtained by imaging surface patterns of objects at predetermined imaging spots before the objects are stored in containers and imaging time instants associated with respective objects having surface patterns respectively during a manufacturing process of the objects;
    a container information acquisition unit configured to acquire container identification information identifying the containers containing the objects and associated time ranges during which the objects are stored in the containers; and
    a registration unit configured to register the container identification information corresponding to surface pattern image information acquired by the object information acquisition unit associated with respective objects based on a time difference from the imaging of the objects to the storing in the container, the imaging time instants associated with the surface pattern image information of the objects and the time ranges associated with container identification information of containers containing the objects.

2. The object information management system according to claim 1, further comprising:
    a calculation unit configured to calculate the time difference based on a distance from the imaging spot to a storing spot in the container and conveyance speed of the objects during the manufacturing process.

3. The object information management system according to claim 1,
    wherein the object information acquisition unit is further configured to acquire manufacture information concerning the manufacturing process of the objects associated with surface pattern image information obtained by imaging surface patterns of the objects,
    wherein the container information acquisition unit is further configured to acquire shipping information concerning the shipping of the containers associated with container identification information of the containers, and
    wherein the registration unit is configured to register the container identification information corresponding to surface pattern image information acquired by the object information acquisition unit associated with the manufacture information associated with the surface pattern image information and shipping information associated with the container identification information.

4. The object information management system according to claim 1, further comprising:
    a receiving unit configured to receive a taken image obtained by imaging the surface pattern of an object as an identification target and container identification information of a container containing the object;
    an extraction unit configured to extract image information registered by being associated with container identification information received by the registration unit; and an output unit configured to output a result obtained by respectively checking the image information extracted by the extraction unit with the received taken image.

5. The object information management system according to claim 1, further comprising:
a shipping container information acquisition unit configured to acquire shipping container identification information, for identifying shipping containers for shipping to which objects stored in the container in the manufacturing process are moved, associated with the container identification information of containers,
wherein the registration unit is configured to register the container identification information corresponding to the surface pattern image information acquired by the object information acquisition unit and the shipping container identification information acquired by the shipping container information acquisition unit associated with the container identification information by associating these information to each other.

6. The object information management system according to claim 5, further comprising:
a receiving unit configured to receive a taken image obtained by imaging the surface pattern of an object as an identification target and shipping container identification information of a shipping container containing the object;
an extraction unit that configured to extract image information registered by being associated with shipping container identification information received by the registration unit; and
an output unit configured to output a result obtained by respectively checking the image information extracted by the extraction unit with the received taken image.

7. An object information management method comprising:
acquiring surface pattern image information obtained by imaging surface patterns of objects at predetermined imaging spots before the objects are stored in containers and imaging time instants associated with respective objects having surface patterns respectively during a manufacturing process of the objects;
acquiring container identification information identifying the containers containing the objects and associated time ranges during which the objects are stored in the containers; and
registering the container identification information corresponding to the acquired surface pattern image information associated with respective objects based on a time difference from the imaging of the objects to the storing in the container, the imaging time instants associated with the surface pattern image information of the objects and the time ranges associated with container identification information of containers containing the objects.

8. A non-transitory computer readable medium storing a program causing a computer to execute a process for managing an object information, the process comprising:
acquiring surface pattern image information obtained by imaging surface patterns of objects at predetermined imaging spots before the objects are stored in containers and imaging time instants associated with respective objects having surface patterns respectively during a manufacturing process of the objects;
acquiring container identification information identifying the containers containing the objects and associated time ranges during which the objects are stored in the containers; and
registering the container identification information corresponding to the acquired surface pattern image information associated with respective objects based on a time difference from the imaging of the objects to the storing in the container, the imaging time instants associated with the surface pattern image information of the objects and the time ranges associated with container identification information of containers containing the objects.

* * * * *